(12) United States Patent
Hariharesan et al.

(10) Patent No.: US 9,468,716 B2
(45) Date of Patent: Oct. 18, 2016

(54) CASSETTE WITH INFUSION SET CONTAINING SPRING-BIASED ANTI-FREEFLOW MECHANISM FOR PERISTALTIC INFUSION PUMP

(75) Inventors: Seralaathan Hariharesan, Flower Mound, TX (US); James Allen Higgins, Plano, TX (US); David Woodruff West, McKinney, TX (US)

(73) Assignee: NESTEC S.A., Vevey (CH)

( * ) Notice: Subject to any disclaimer, the term of this patent is extended or adjusted under 35 U.S.C. 154(b) by 820 days.

(21) Appl. No.: 13/393,059

(22) PCT Filed: Jul. 8, 2010

(86) PCT No.: PCT/US2010/041323
§ 371 (c)(1),
(2), (4) Date: Apr. 30, 2012

(87) PCT Pub. No.: WO2011/025589
PCT Pub. Date: Mar. 3, 2011

(65) Prior Publication Data
US 2012/0266965 A1 Oct. 25, 2012

Related U.S. Application Data

(60) Provisional application No. 61/238,386, filed on Aug. 31, 2009.

(51) Int. Cl.
| | | |
|---|---|---|
| *A61M 39/28* | (2006.01) | |
| *F16K 7/06* | (2006.01) | |
| *A61M 5/142* | (2006.01) | |

(52) U.S. Cl.
CPC ........ *A61M 5/14232* (2013.01); *A61M 39/281* (2013.01); *A61M 39/284* (2013.01);
(Continued)

(58) Field of Classification Search
CPC .... F16K 7/063; F16K 7/065; A61M 39/281; A61M 39/284; A61M 2205/128
USPC ........... 251/4, 5, 7, 8, 9; 414/440, 441, 476, 414/477.2, 479, 480; 604/151, 250; 267/155
See application file for complete search history.

(56) References Cited

U.S. PATENT DOCUMENTS 2,816,339 A * 12/1957 Prete, Jr. ................ A44B 11/14
24/170
4,355,783 A * 10/1982 Morin ..................... F16K 7/065
251/9

(Continued)

FOREIGN PATENT DOCUMENTS

EP 0483794 A1 5/1992
EP 0718001 A2 6/1996
(Continued)

OTHER PUBLICATIONS

International Preliminary Report on Patentability for corresponding International Application No. PCT/US2010/041323 mailed on Mar. 15, 2012.
(Continued)

*Primary Examiner* — Mary McManmon
*Assistant Examiner* — Jonathan Waddy
(74) *Attorney, Agent, or Firm* — K&L Gates LLP

(57) ABSTRACT

Flow control devices.—In a general embodiment, the present disclosure provides a cassette (30) comprising a housing having a flow restrictor (34), and a tube (36) attached to the housing and positioned adjacent the flow restrictor. The flow restrictor may be so constructed and arranged to rotate from a first position in which the flow restrictor prevents fluid flow through the tube to a second position in which fluid is able to flow through the tube when the cassette is positioned inside a pumping device. As a result, the cassette is designed to prevent free flow of fluid when an enteral feeding tube set is not installed in a pumping device.

3 Claims, 4 Drawing Sheets

(52) U.S. Cl.
CPC ......... *F16K 7/063* (2013.01); *A61M 2205/12* (2013.01); *A61M 2205/128* (2013.01); *A61M 2205/6045* (2013.01); *Y10T 137/0318* (2015.04)

(56) References Cited

U.S. PATENT DOCUMENTS

| | | | |
|---|---|---|---|
| 5,257,978 A | | 11/1993 | Haber et al. |
| 5,300,043 A | * | 4/1994 | Devlin et al. ................. 604/250 |
| 5,904,668 A | | 5/1999 | Hyman et al. |
| 5,954,485 A | * | 9/1999 | Johnson et al. ............. 417/474 |
| 8,308,457 B2 | * | 11/2012 | Rotem et al. ................. 417/479 |
| 8,986,252 B2 | * | 3/2015 | Cummings ....... A61M 5/14232 417/477.2 |
| 2007/0269324 A1 | * | 11/2007 | Goldor et al. ................ 417/474 |
| 2008/0095649 A1 | | 4/2008 | Ben-Shalom et al. |

FOREIGN PATENT DOCUMENTS

| | | |
|---|---|---|
| EP | 1557187 A1 | 7/2005 |
| JP | 2004166901 | 6/2004 |
| JP | 3133453 | 6/2007 |
| WO | 98/13080 | 4/1998 |

OTHER PUBLICATIONS

Written Opinion and International Search Report mailed Dec. 27, 2010 for corresponding Intl. Appln. No. PCT/US2010/041323.

\* cited by examiner

CASSETTE WITH INFUSION SET CONTAINING SPRING-BIASED ANTI-FREEFLOW MECHANISM FOR PERISTALTIC INFUSION PUMP

CROSS REFERENCE TO RELATED APPLICATIONS

The present application is a National Stage of International Application No. PCT/US2010/041323, filed on Jul. 8, 2010, which claims priority to U.S. Provisional Patent Application No. 61/238,386, filed on Aug. 31, 2009, the entire contents of which are being incorporated herein by reference.

BACKGROUND

The present disclosure generally relates to health and nutrition. More specifically, the present disclosure relates to flow control devices and methods of using the flow control devices.

The delivery of nutritional compositions to mammals, such as human patients, that cannot orally ingest food or other forms of nutrition is often of critical importance. For example, enteral bottles and containers having feeding tubes that deposit food directly into the gastrointestinal tract at a point below the mouth are often used to sustain life while a patient is unable, or refuses, to take food orally. Bottles and containers, feeding tubes and other artificial delivery systems and routes can be used temporarily during the treatment of acute medical conditions. For chronic medical conditions, such systems and routes can be used as part of a treatment regimen that lasts for the remainder of a patient's life. No matter the duration of use, these devices often provide the only means for feeding the patient.

The use of enteral feeding pumps, in conjunction with an enteral feeding tube set as part of an enteral feeding system, for the administering of medical fluids is also well known in the medical arts. The enteral feeding tube set will typically include several long sections of tubing, connected to a centralized, shorter section of tubing. One common concern with the enteral feeding tube set is that fluid flow from a nutritional source through the enteral feeding tube set may begin before the feeding tube set is connected to an enteral administration pump. As a result, the nutritional fluid may spill out of the tube set or be administered to a patient before the desired time.

SUMMARY

The present disclosure relates to flow control devices and methods of using the flow control devices. In a general embodiment, the present disclosure provides a cassette including a housing having a flow restrictor including a locking member and a spring, and a tube attached to the housing and positioned adjacent the flow restrictor. The flow restrictor acts to occlude the tube and form a flow restriction mechanism in the cassette.

In an embodiment, the tube includes a first end attached to an inlet port and a second end attached to an outlet port. Any suitable portion of the tube can be flexible. In this regard, the cassette can be part of an enteral feeding tube set that includes tubing connected to the nutritional composition and to a person receiving the nutritional composition. The cassette is designed to prevent free flow of fluid through the feeding tube set when the feeding tube set is not installed in a pumping device.

In an embodiment, the flow restrictor includes a locking member and a spring in combination with a peg that is attached to the housing. The locking member of the flow restrictor is constructed and arranged to rotate from a first position that occludes the tube to a second position that allows fluid to flow through the tube when inserted into a pumping device. As a result, the flow restriction mechanism can be disengaged (e.g., allow fluid flow) for manual priming of the tube set and disengaged when the feeding tube set is installed into a pumping device.

In an embodiment, the cassette further includes a stopper attached to the housing and positioned adjacent the tube and on an opposite side of the tube from the flow restrictor. The flow restrictor and the stopper operate in conjunction to occlude the tube when the flow restrictor is in a resting position and to allow fluid to flow through the tube when the flow restrictor is in an actuated position.

In another embodiment, the present disclosure provides a flow control system including a pumping device having a projection and a cassette removably attached to the pumping device. The projection may be an actuation member. The cassette includes a housing having a flow restrictor so constructed and arranged to align with the projection or, in an embodiment, the actuation member, when the cassette is inserted into the pumping device. A flexible tube is attached to the housing and positioned adjacent the flow restrictor. The alignment of the flow restrictor and the projection, or actuation member, causes actuation of the flow restrictor. In an embodiment, the actuation of the flow restrictor includes rotation of the flow restrictor. The flow restrictor may include a locking member and a spring. The flow restrictor may further include a peg attached to the housing. The locking member of the flow restrictor may include an occluding portion and an actuating portion.

In an embodiment, the flexible tube can include a first end attached to an inlet port and a second end attached to an outlet port. Any suitable portion of the tube can be flexible.

In yet another embodiment, the present disclosure provides a method of controlling fluid flow in a tube. The method includes providing a cassette including 1) a housing having a flow restrictor and a stopper, and 2) a tube attached to the housing and positioned adjacent the flow restrictor. Fluid flow is occluded through the tube by positioning an occluding portion of the flow restrictor at a location proximate the stopper. The method further comprises passing fluid through the tube by positioning the occluding portion of the flow restrictor at a location away from the stopper.

In an embodiment, the occluding portion of the flow restrictor is positioned at a location away from the stopper when the cassette is positioned inside a pumping device. For example, an actuating portion of the flow restrictor may be contacted by an actuation member of the pumping device to rotate the flow restrictor. When the flow restrictor is rotated, the occluding portion is also rotated to a location away from the stopper, which allows fluid to flow through the flexible tube.

An advantage of the present disclosure is to provide an improved flow control device.

Another advantage of the present disclosure is to provide an improved enteral feeding cassette having a flow restriction mechanism.

Yet another advantage of the present disclosure is to provide an improved method of preventing fluid flow through an enteral feeding cassette when the cassette is not attached to a pumping device.

Still another advantage of the present disclosure is to provide an improved method of controlling flow during enteral feeding.

Additional features and advantages are described herein, and will be apparent from the following Detailed Description and the figures.

DETAILED DESCRIPTION

The present disclosure relates to flow control devices and methods of using the flow control devices. In a general embodiment, the present disclosure provides a cassette including a housing having a flow restrictor, and a tube attached to the housing and positioned adjacent the flow restrictor. The flow restrictor may include a locking member in combination with a spring and/or a peg that is attached to the housing. In this configuration, the locking member of the flow restrictor is so constructed and arranged to rotate from a first position that restricts fluid flow through the tube to a second position that allows fluid to flow through the tube. The arrangement of the locking member in the first position restricts fluid flow through the tube when the cassette is not in use. The cassette can be part of an enteral administration device or system that administers nutritional compositions to a person or patient in need of same.

The cassette that includes the flow restriction mechanism provides the user an elegant way to install the flow restriction mechanism and feeding tube set into a pumping device via features built into a housing of the cassette and may also provide other built in functionality for successful delivery of the nutritional composition to a person or patient. The flow restriction mechanism prevents leakage/flow of the nutritional composition in the enteral feeding tube set, for example, in the following instances: 1) before and after the feeding tube set is primed with the feeding fluid, 2) during the loading and unloading of the feeding tube set into and out of the pumping device and 3) after the feeding tube set has been removed from the pumping device.

As used herein, the term "nutritional composition" includes, but is not limited to, complete nutritional compositions, partial or incomplete nutritional compositions, and disease or condition specific nutritional compositions. A complete nutritional composition (i.e., those which contain all the essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as a nutritional supplements.

Figure 1:
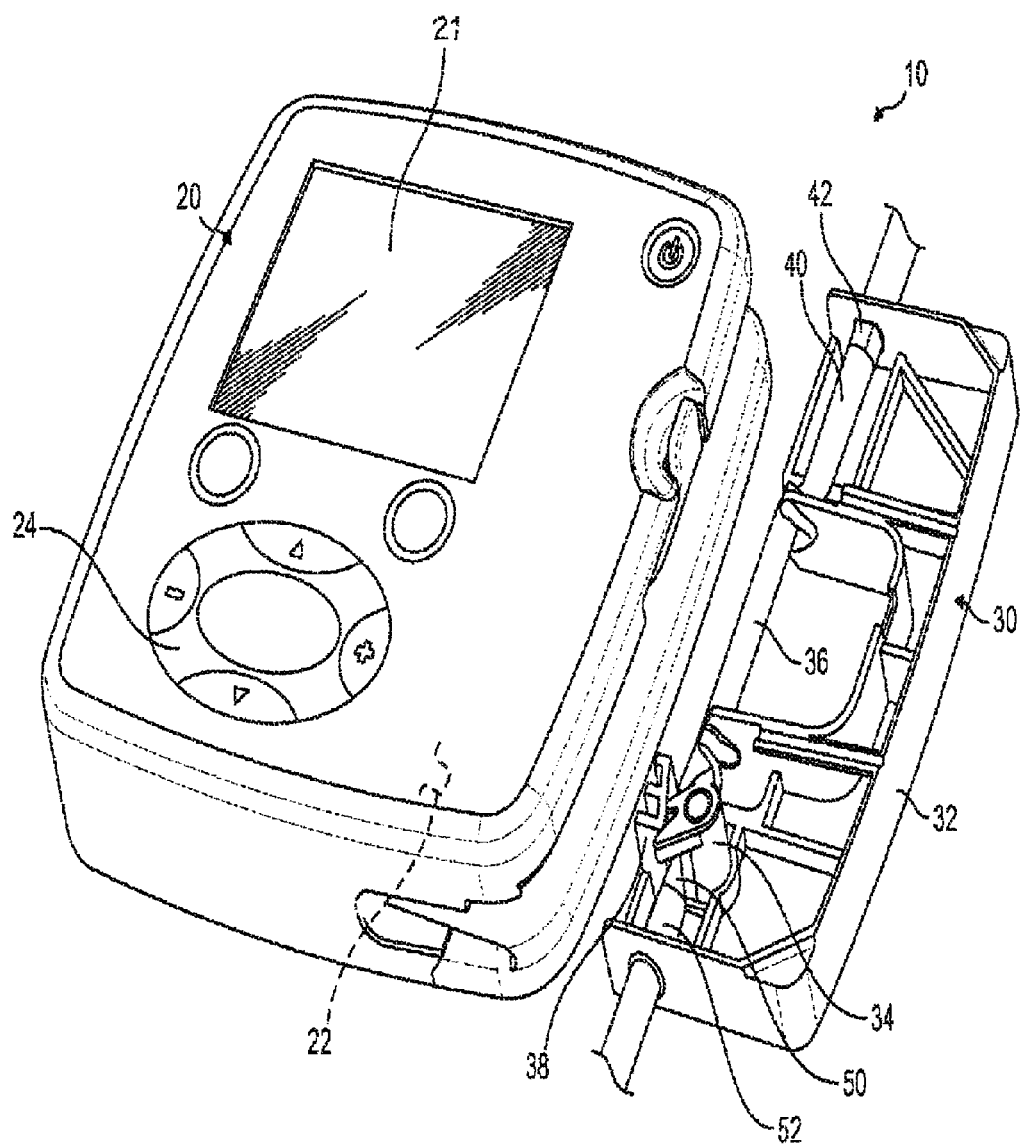
FIG. 1 shows a pumping device and a cassette having a flow restriction mechanism in an embodiment of the present disclosure.
Figure 2:
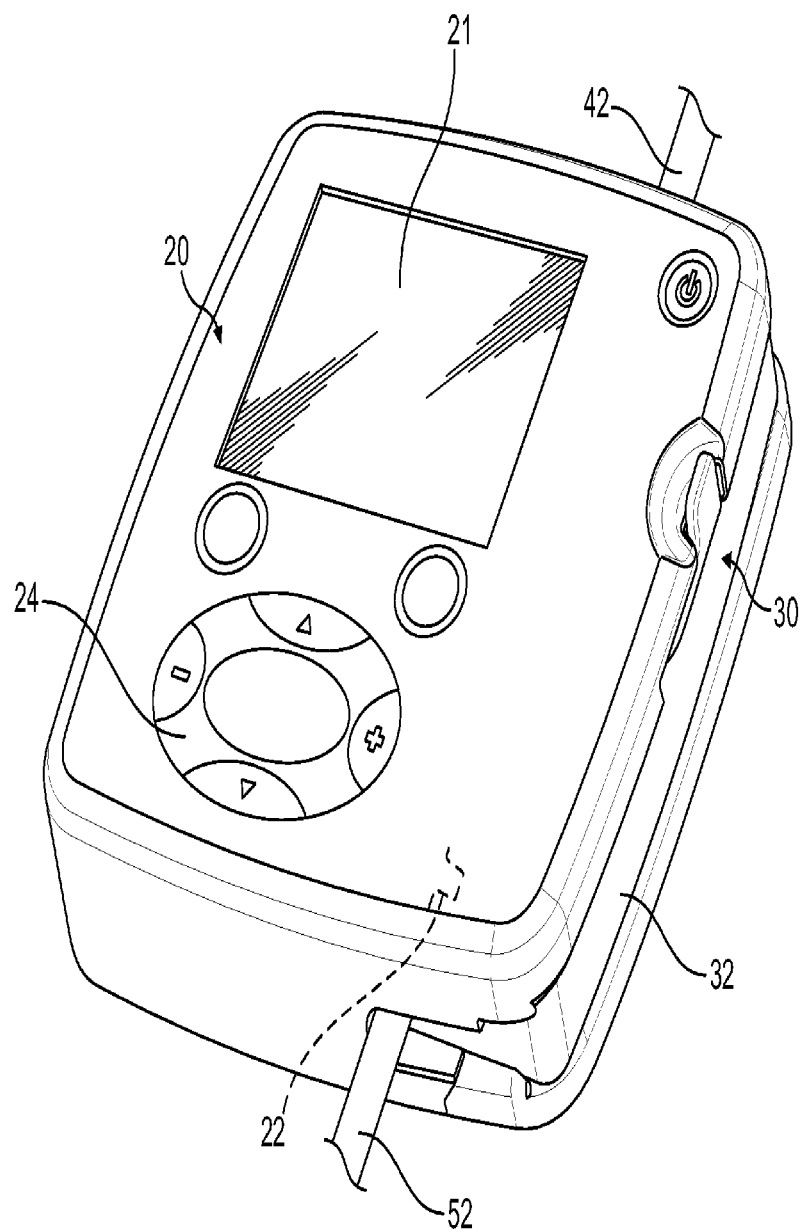
FIG. 2 shows the pumping device and the cassette of FIG. 1 with the cassette inserted into the pumping device.

In an embodiment illustrated in FIGS. 1-2, the present disclosure provides a flow control system 10 including a pumping device 20 having an actuation member 22. Flow control system 10 further includes a cassette 30 removably attached to pumping device 20. The design of cassette 30 can help in loading an enteral feeding tube set (not shown) into pumping device 20 without having to route/guide the tubes or stretch the tubes from the tube set over a rotor (e.g., part of a peristaltic pump).

Pumping device 20 can be an enteral feeding pump. Non-limiting examples of pumping devices are described in U.S. Pat. No. 6,659,976, which is incorporated herein by reference. Pumping device 20 can include a monitor/information screen 21 and a control pad 24 for operating pumping device 20.

Figure 3:
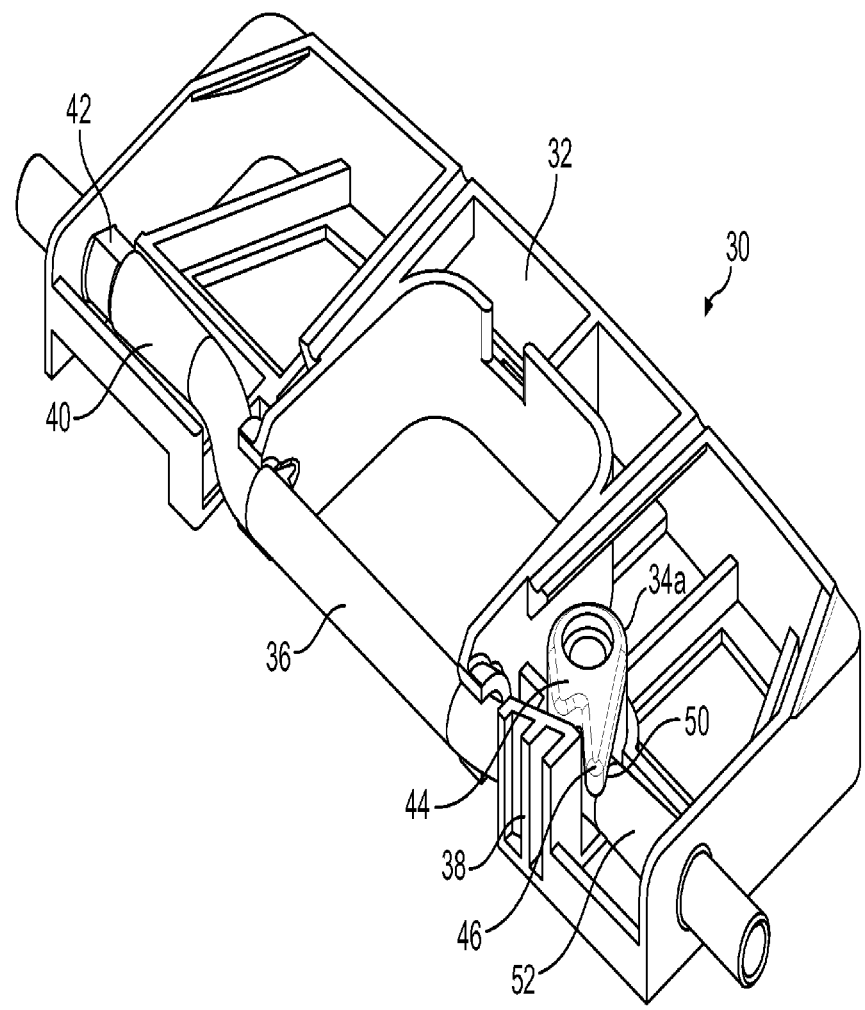
FIG. 3 shows a cassette having a flow restriction mechanism in an embodiment of the present disclosure.
Figure 4:
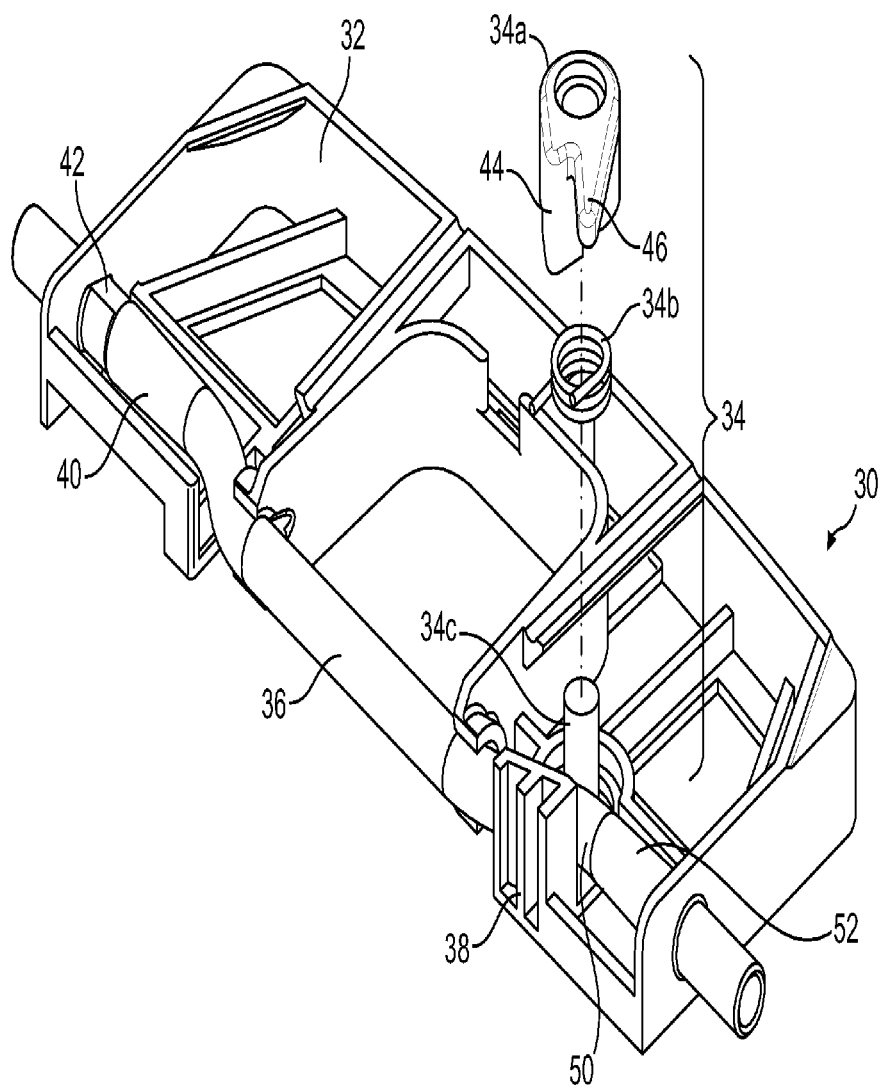
FIG. 4 shows an exploded view of a cassette having a flow restriction mechanism in an embodiment of the present disclosure.

Cassette 30 can have any suitable shape such as the one shown in FIGS. 1 and 3-4 and is design to be positioned within pumping device 20. Non-limiting examples of alternative cassette configurations are described in U.S. Pat. Nos. D504,506, D505,199, D455,489, D501,924 and D507,647, which are incorporated herein by reference. Cassette 30 can be made from any suitable rigid, semi-rigid or flexible material. Cassette 30 can also be "keyed/poka yoked" such that it can be inserted into pumping device 20 only one way.

As illustrated in FIGS. 1-2, cassette 30 includes a housing 32 having a flow restrictor 34 constructed and arranged to align with actuation member 22 of pumping device 20 when cassette 30 is inserted into pumping device 20. Housing 32 further includes a stopper 38 located or positioned adjacent flexible tube 36 on a side of flexible tube 36 opposite flow restrictor 34. Flexible tube 36 is attached to housing 32 and positioned adjacent flow restrictor 34. Flexible tube 36 can be made of any suitable materials such as silicone. It should be appreciated that any suitable portion of flexible tube 36 can be flexible while the remaining portion is rigid or semi-rigid.

Flexible tube 36 can include a first end 40 attached to an inlet port 42 and a second end 50 attached to an outlet port 52. As a result, fluid can flow through flexible tube 36 in the direction from first end 40 to second end 50. Inlet port 42 can be attached to a tube connected to a nutritional composition source. Outlet port 52 can be attached to a tube connected to the person receiving the nutrition composition.

As is shown in FIG. 4, in an embodiment, flow restrictor 34 includes a locking member 34a, a spring 34b and a peg 34c that is attached to housing 32. Locking member 34a includes an occluding portion 44 and an actuating portion 46. As mentioned above, flow restrictor 34 is so constructed and arranged to align with actuation member 22 of pumping device 20. Specifically, actuating portion 46 of flow restrictor 34 is so constructed and arranged to be contacted by actuation member 22 to rotate flow restrictor 34. Although shown as substantially rectangular in shape, actuation member 22 may have any shape or size that is sufficient to contact and rotate flow restrictor 34. For example, actuation member 22 may have a shape that is square, rectangular, triangular, oblong, parabolic, etc. Likewise, it will also be understood that actuating portion 46 of flow restrictor 34 may have any shape or size that is sufficient to be contacted and rotated by actuation member 22. For example, actuating portion 46 may have a shape that is square, rectangular, triangular, oblong, parabolic, etc. Further, the skilled artisan will also appreciate that occluding portion 44 of flow restrictor 34 may have any shape or size that is sufficient to occlude flexible tube 36 by pressing flexible tube 36 against stopper 38. For example, actuating portion 46 may have a shape that is square, rectangular, triangular, oblong, parabolic, etc.

During operation, when cassette 30 is inserted into pumping device 20, actuation member 22 will contact actuating portion 46 of locking member 34a. Upon continued insertion into pumping device 20, actuation member 22 will actuate flow restrictor 34. In an embodiment, actuation member 22 actuates flow restrictor 34 by pushing actuating portion 46 of locking member 34a in a direction that is away from pumping device 20 to rotate locking member 34a counter-clockwise. Locking member 34a and spring 34b rotate about a common axis of rotation that is shared with peg 34c. The skilled artisan will appreciate that locking member 34a need not rotate counter-clockwise. Rather, in another embodiment, locking member 34a may rotate clockwise.

In an embodiment where flow restrictor 34 is actuated by rotation, flow restrictor 34 rotates from a first, or resting position, as shown in FIGS. 1 and 3, to a second, or actuated position (not shown) as cassette 30 is inserted into pumping device 20. In the first, or resting position, flow restrictor 34 is located proximate stopper 38. By "located proximate stopper 38," it is understood that at least a portion of flow restrictor 34 is positioned close enough to stopper 38 to prevent fluid from flowing through flexible tube 36. Accordingly, when flow restrictor 34 is in a first or resting position and spring 34b is in a corresponding biased position, an occluding portion 44 of locking member 34a may press flexible tube 36 against stopper 38 so as to occlude flexible tube 36 and prevent fluid flow therethrough. Cassette 30 may be in the first, or resting position prior to insertion of cassette 30 into pumping device 20, and after cassette 30 is removed from pumping device 20.

As previously discussed, as cassette 30 is inserted into pumping device 20, actuation member 22 contacts actuating portion 46 of locking member 34a. Upon continued insertion into pumping device 20, actuation member 22 will continue to act upon actuating portion 46 of locking member 34a to rotate locking member 34a to a second, actuated position (not shown), thereby applying tension to spring 34b and moving occluding portion 44 of locking member 34a away from stopper 38 such that flow restrictor 34 is located away from stopper 38. By "located away from stopper 38," it is understood that flow restrictor 34 is positioned sufficiently far enough away from stopper 38 to allow fluid to flow through flexible tube 36. Accordingly, when flow restrictor 34 is in an actuated position, occluding portion 44 of locking member 34a does not occlude flexible tube 36 against stopper 38 and, therefore, allows fluid to flow therethrough.

When cassette 30 is fully inserted into pumping device 20, actuation member 22 remains in contact with actuating portion 46 of locking member 34a to allow fluid to flow through flexible tube 36 during the time that cassette 30 resides in pumping device 20. As cassette 30 is removed from pumping device 20, actuation member 22 loses contact with actuating portion 46 of locking member 34a allowing the tension on spring 34b to relax. As the tension on spring 34b relaxes, spring 34b and locking member 34a are allowed to return to the first, or resting, position. In an embodiment, the locking member 34a and spring 34b relax and rotate clockwise until actuating portion 46 of locking member 34a contacts stopper 38, which prevents further clockwise rotation of locking member 34b. Accordingly, when cassette 30 is removed from pumping device 20, flow restrictor 34 moves to the first, relaxed position, which occludes flexible tube 36.

As a result, flow restrictor 34 can be unlocked and deactivated by pumping device 20 when cassette 30 is inserted in pumping device 20 and reactivated when it is removed from pumping device 20. Unlike conventional anti-free flow devices in existing enteral feeding tube sets, cassette 30 is not deactivated by closing a door, by pressure, or a roller clamp. Instead, it will be deactivated by physically rotating flow restrictor 34 via a feature in pumping device 20.

In sum, the flow restriction mechanism of cassette 30 can be activated by a bias on spring 34b and deactivated via application of tension to spring 34b by rotating locking member 34a. The locking member 34a, which works in conjunction with the bias of spring 34b, will seal the flow path thereby preventing flow through flexible tube 36. This flow restriction mechanism prevents any static pressure loss during pumping. When cassette 30 is inside pumping device 20, the flow can be prevented/controlled by pump rollers (e.g., peristaltic pumps) within pumping device 20.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A flow control system comprising:
   a pumping device comprising an actuation member;
   a cassette removably attached to the pumping device, the cassette comprising a housing and a flow restrictor comprising (i) a locking member, (ii) one peg that is attached to the housing, and (iii) a spring, the flow restrictor constructed and arranged to align with the actuation member when the cassette is positioned within the pumping device; and
   a flexible tube positioned adjacent the flow restrictor and a stopper that is positioned on an opposite side of the flexible tube from the flow restrictor, the flexible tube comprising a first end attached to an inlet port and a second end attached to an outlet port of the housing, the locking member is constructed and arranged to rotate from a first resting position that restricts fluid flow through the flexible tube to a second actuated position that allows fluid to flow through the flexible tube, the locking member and the spring rotate about a common axis of rotation that is shared with the one peg, and the locking member houses the spring and includes an actuating portion and an occluding portion, the actuating portion rotating the locking member,
   the actuating portion of the locking member and the actuation member of the pumping device are configured and arranged such that when the cassette is inserted into the pumping device, the actuating portion contacts the actuation member, and the actuation member is further configured and arranged to, when the cassette is continued to be inserted in the pumping device, push the actuating portion in a direction away from the stopper to rotate the locking member on the spring from the first resting position in which the occluding portion of the locking member is located proximate the stopper to the second actuated position in which the locking member applies tension to the spring, and the occluding portion of the locking member is moved away from the stopper.

2. The flow control system of claim 1, wherein the actuation member is a projection.

3. A method of controlling fluid flow in a flexible tube, the method comprising:
   providing a cassette comprising a housing and a flow restrictor comprising (i) a locking member, (ii) one peg that is attached to the housing, and (iii) a spring, the housing further comprising a stopper, the flexible tube positioned adjacent the flow restrictor and the stopper that is positioned on an opposite side of the flexible tube from the flow restrictor, and the flexible tube comprising a first end attached to an inlet port and a second end attached to an outlet port of the housing, the locking member is constructed and arranged to rotate from a first resting position that restricts fluid flow through the flexible tube to a second actuated position that allows fluid to flow through the flexible tube, the locking member and the spring rotate about a common axis of rotation that is shared with the one peg, and the locking member houses the spring and includes an actuating portion and an occluding portion, the actuating portion rotating the locking member;

occluding fluid flow through the flexible tube by positioning the occluding portion at a location proximate the stopper and passing fluid through the flexible tube by positioning the occluding portion at a location away from the stopper, the occluding comprising:

inserting the cassette into a pumping device, such that the actuating portion of the locking member is brought into contact with an actuation member of the pumping device, and continued insertion of the cassette into the pumping device comprises the actuation member pushing the actuating portion in a direction away from the stopper to rotate the locking member on the spring from the first resting position in which the occluding portion of the locking member is located proximate the stopper to the second actuated position in which the locking member applies tension to the spring and the occluding portion of the locking member is moved away from the stopper.

\* \* \* \* \*